United States Patent [19]

Klawitter

[11] 4,357,715

[45] Nov. 9, 1982

[54] HEART VALVE PROSTHESIS

[75] Inventor: Jerome J. Klawitter, New Orleans, La.

[73] Assignee: Hemex Incorporated, Austin, Tex.

[21] Appl. No.: 198,446

[22] Filed: Oct. 20, 1980

Related U.S. Application Data

[63] Continuation-in-part of Ser. No. 111,488, Jan. 14, 1980, Pat. No. 4,328,592.

[51] Int. Cl.³ .............................................. A61F 1/22
[52] U.S. Cl. ..................................... 3/1.5; 137/512.1; 137/527.8
[58] Field of Search .................. 3/1.5; 137/512.1, 527, 137/527.8

[56] References Cited

U.S. PATENT DOCUMENTS

| | | | |
|---|---|---|---|
| 3,589,392 | 6/1971 | Meyer | 137/525.1 |
| 3,903,548 | 9/1975 | Nakib | 3/1.5 |
| 4,078,268 | 3/1978 | Possis | 3/1.5 |
| 4,159,543 | 7/1979 | Carpentier | 3/1.5 |
| 4,178,638 | 12/1979 | Meyer | 3/1.5 |
| 4,178,639 | 12/1979 | Bokros | 3/1.5 |
| 4,254,508 | 3/1981 | Bokros | 3/1.5 |
| 4,263,680 | 4/1981 | Reul et al. | 3/1.5 |
| 4,272,854 | 6/1981 | Bokros | 3/1.5 |

FOREIGN PATENT DOCUMENTS

| | | | |
|---|---|---|---|
| 2846299 | 5/1979 | Fed. Rep. of Germany | 3/1.5 |
| 1160008 | 7/1969 | United Kingdom | 3/1.5 |

*Primary Examiner*—Ronald L. Frinks
*Attorney, Agent, or Firm*—Fitch, Even, Tabin, Flannery & Welsh

[57] ABSTRACT

Double-leaflet heart valves having an annular valve body and a pair of leaflets which may be arcuate or flat in cross section. Guides protrude oppositely from the leaflets and are received in complementary depressions in the interior wall surface of the annular valve body at generally diametrically opposite locations. The depressions are preferably elongated so that, as the leaflets pivot between the open and closed positions, the guides move from one end of the elongated depressions to the other. Eccentric pivot axes provide for quick response of the leaflets, and small rounded knobs are received in the depressions which assure the alignment is maintained.

8 Claims, 6 Drawing Figures

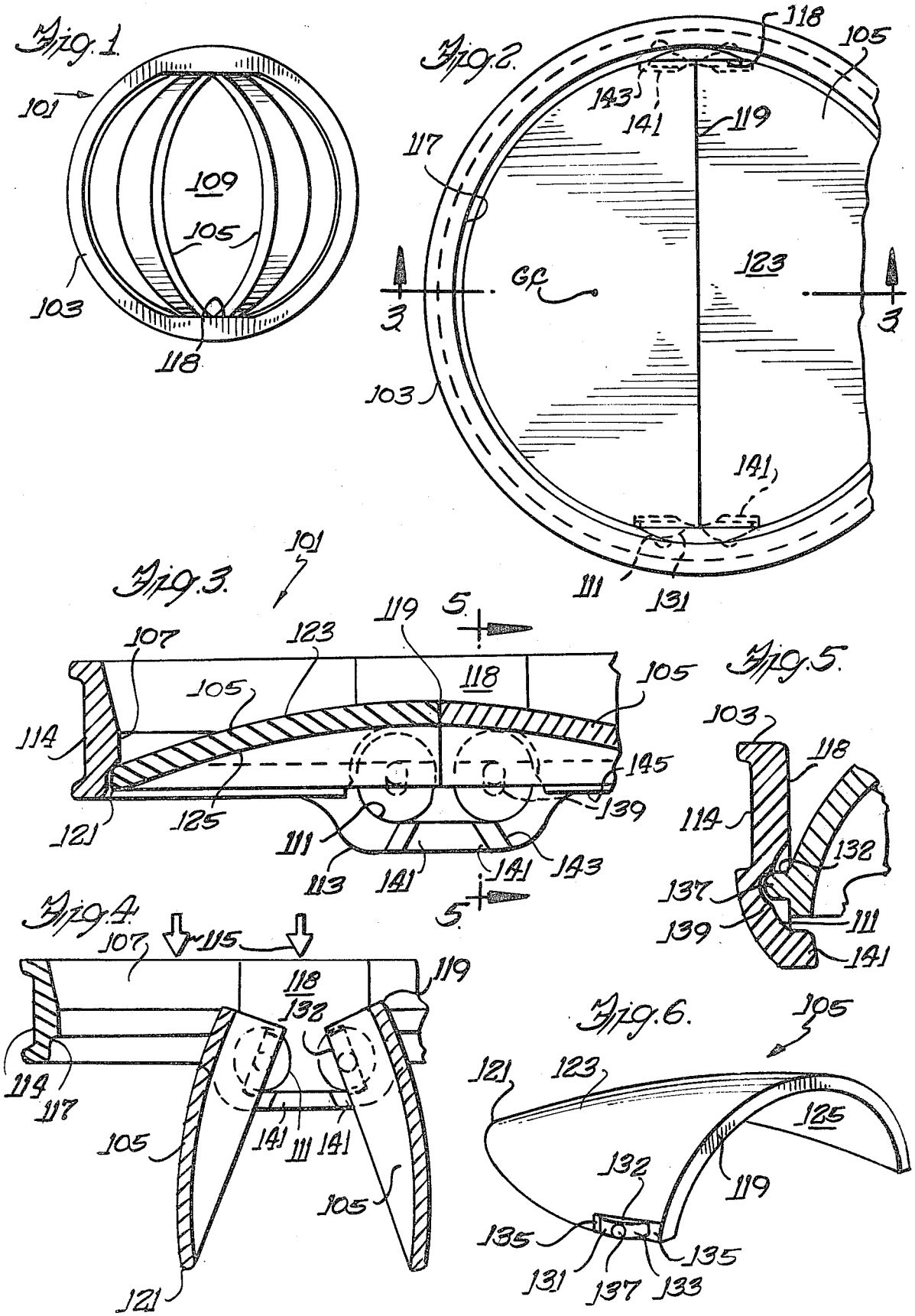

HEART VALVE PROSTHESIS

This application is a continuation-in-part of my copending application Ser. No. 111,488, filed Jan. 14, 1980, now U.S. Pat. No. 4,328,592, issued May 11, 1982.

BACKGROUND OF THE INVENTION

This invention relates to heart valve prostheses for replacement of defective natural valves and more particularly to heart valve prostheses using a pair of pivoting valve members, preferably ones which are arcuate in cross section.

Various types of heart valve prostheses have been developed which operate hemodynamically as a result of the pumping action of the heart. Some of these valves which have been used employ a ball-and-cage arrangement, whereas others have used a disc-type arrangement for the valve member. Exemplary of a disc of the free floating type is U.S. Pat. No. 3,543,411, issued Oct. 20, 1970. Various disc-type valves having a pivotal arrangement have been developed, such as that shown in U.S. Pat. No. 3,546,711 to Bokros, issued Dec. 15, 1970, and that shown in U.S. Pat. No. 3,859,668, issued Jan. 14, 1975.

Disc-type heart valves have also been developed which use two members or leaflets, instead of a single disc, which leaflets rotate about parallel axes as a part of the opening and closing of the valve. British Pat. No. 1,160,008 shows an early version of such a valve, and U.S. Pat. No. 4,078,268, issued Mar. 14, 1978, shows a later version.

SUMMARY OF THE INVENTION

The invention provides improved versions of two-leaflet heart valve prostheses having excellent blood flow characteristics. Guides extend from opposite sides of each of the leaflets and are received in depressions formed in the interior wall surfaces of an annular valve body. The valve members are preferably curved in cross section, and each pivots about an eccentric axis. The depressions are elongated so that the axis of pivot of each leaflet changes relative to the valve body. This movement in the depressions plus the design of the guides prevents blood clotting from beginning in an otherwise stagnant region. The location of the pivot axes slightly downwstream of the orifice defined by the annular valve body, essentially removes them from the region of greatest constriction and provides the valve with excellent flow characteristics. When the valve members are curved, a fairly large central passageway is created which further enhances blood flow therethrough. The heart valves open and close easily and reliably and exhibit excellent resistance to wear.

BRIEF DESCRIPTION OF THE DRAWINGS

FIG. 1 is a plan view of a heart valve prosthesis embodying various features of the invention with the pair of leaflets shown in the open position;

FIG. 2 is a plan view of the heart valve shown in FIG. 1, enlarged in size, with the leaflets shown in the closed position;

FIG. 3 is a fragmentary sectional view taken generally along the line 3—3 of FIG. 2;

FIG. 4 is a sectional view similar to FIG. 3 with the leaflets in the open position;

FIG. 5 is a fragmentary sectional view taken along the line 5—5 of FIG. 3; and

FIG. 6 is a perspective view of one of the leaflets.

DETAILED DESCRIPTION OF PREFERRED EMBODIMENT

Depicted in the drawings is a bi-leaflet heart valve 101 which includes an annular valve body 103 and a pair of pivoting leaflets 105 which are curved in cross section but which might be made flat if desired. The annular body 103 has an internal surface 107 which defines a central passageway 109 of substantially circular cross section. The leaflets 105 are supported about eccentric axes in generally diametrically opposed depressions 111 formed in the interior wall 107 of the annular valve body and extending into a pair of standards 113 which depend in a downstream direction from the main ring portion of the annular body.

The annular body 103 has the usual groove 114 formed in its outer periphery to accept a suturing ring, and the interior surface 107 optionally tapers inwardly slightly from its upper end to provide a smooth entrance region for the blood which, in the open position, flows downward therethrough in the direction of the arrows 115 in FIG. 4. A seat 117 is formed in the lower region of the interior surface as discussed hereinafter. The depressions 111 are elongated and are located in a pair of flat or planar wall sections 118 formed in the valve body which extend downward into the region of the diametrically opposite standards 113.

The leaflets 105 may be flat but preferably are arcuate or curved in cross section, as best seen in FIGS. 1 and 3, and have a nominally uniform thickness along the upstream and downstream edges. The leaflets may have the general shape of a section that has been cut from a tube of elliptical cross section; however, in the illustrated, preferred embodiment, the leaflets 105 have the general shape of a portion of a hollow sphere so that, when in the closed position shown in FIG. 3, they together form a sector of such a hollow sphere. The upstream edge (FIG. 4) is referred to as the minor edge 119 because it is shorter in length than the downstream edge which is referred to as the major edge 121. The convex surface 123 of the leaflet faces upstream in the closed position, and the concave surface 125 faces downstream. The upstream edges 119 are substantially planar and are oriented with respect to the downstream and upstream surfaces so as to squarely abut each other in the closed position, as illustrated in FIG. 3.

The intersection between each curved leaflet 105 and the right circular cylindrical interior wall surface 107 in the region of the seat is that of a segment of a circle. The major edge 121 has the outline of nearly a complete semicircle and seals the passageway 109 when it engages the seat 117. The surface of the seat 117 faces generally downstream and may have a radius of curvature just slightly greater than the radius of curvature of the major edge 121 at the upstream surface 123, so that there is only line contact between it and the seat to reduce blood cell crushing (hemolysis).

The pivotal axis for each of the leaflets 105 is eccentric to the leaflet and also to the centerline through the passageway 109, and these axes are defined by a pair of oppositely extending guides 131 carried by each leaflet which have generally parallel side surfaces 132 with terminal surfaces 133 that are preferably sections of a spherical surface. The surfaces 133 are referred to as spheriodal because, in addition to being generally spherical, they may also be paraboliodal or hyperboloidal. The guides 131 are formed at opposite lateral locations on the arcuate leaflets 105 which are flanked by planar regions 135 (FIG. 6). The guides 131 are received within the elongated depressions 111 which have a radius of curvature slightly larger, e.g., about 2%, than that of the spherical surfaces 133. A small rounded knob 137, which is preferably a sector of a sphere, is formed centrally of each of the surfaces 133 fo a purpose explained hereinafter.

The elongated depressions 111 are aligned somewhere between the vertical, i.e., parallel to the axis of the passageway 109, and at a downstream angle thereto of not more than about 60°. In the illustrated valve, the centerline of the elongated depressions is parallel to a vertical plane through the valve center line. Because the radius of curvature of the depressions is greater than that of the spherical surfaces, the ends of the guides 131 do not touch the deepest points of the depressions, as can be seen by the exaggerated illustration in FIG. 5. Instead, the flanking flat surfaces 135 serve as the thrust bearing surfaces and rotate against the flat surfaces 118 of the valve body. The knobs 137 are received in central slots 139.

Each depression 111 preferably has a total length which is at least about 110% of its transverse (horizontal in FIG. 3) dimension and thus has a central cylindrical surface, whereby movement of the guides 131 within the depressions, coupled with the flow of blood therepast, washes the entire concave surface of the depressions and serves as a positive deterrent to clotting. The orientation of the leaflets 105 in the open position is determined by stops 141 which each have a pair of generally outward-facing surfaces 143 against which complementary surfaces 145 formed on the leaflets 105 abut. The leaflets rotate about 70° from the closed position to the open position illustrated in FIG. 4 where they are tilted somewhat with respect to the flow path through the passageway. For a valve designed to operate as an aortic valve, the amount of rotation may be only about 60°. Generally, the lesser the rotation, the more prompt is the response of the leaflets in moving to the closed position, and leaflets in a mitral valve may rotate only as few as about 55°.

As soon as blood flow through the valve in the direction of the arrows 115 ceases upon the ending of the pumping stroke of the respective ventricle for an aortic valve, back pressure builds up in the aorta causing blood to attempt to flow backward through the valve 101. The backflow exerts a dragging force on the surfaces of the leaflets which is amplified by the composite moment arm (about which the major surface portions of the leaflets are offset from the pivotal axis) and promptly causes the leaflets 105 to begin to pivot upward from their positions shown in FIG. 4 while the guides 131 simultaneously move upward in the elongated depressions 111.

The location of the arcuate seats 117 provided in the interior surface 107 of the valve body is such, relative to the location of the depressions 111, that the closing movement of the leaflets is halted when the major edges 121 contact the downstream-facing surface of the seats 117. Furthermore, the location is such that, when the major edges 121 are in contact with the seats 117 and the minor edges 119 are abutting each other, the guides 131 and the knobs 137 are spaced slightly below the uppermost locations in the depressions 111 and in the slots 139 and are thus unloaded, eliminating the propensity for wear at these locations during the duration of closure when the force against the leaflets is at its greatest. This spacing of the spherical surfaces of the guides 131 slightly below the uppermost locations they might occupy in the depressions 111 is a stable position because of the strategic location of the arcuate seats 117. In this respect, the geometric center of the leaflets is indicated in FIG. 2 by the point labeled GC, and the seat 17 extends substantially past a line through the point GC so the seat flanks the geometric center of each leaflet in the closed position. Accordingly, the force against the leaflet's downstream surface 125 is borne by the donwstream-facing surface of the seat 117 and thus assures that the guides 131 remain unloaded in the closed position.

As soon as the next pumping stroke is ready to begin, the back pressure on the downstream surfaces 125 of the leaflets is removed, and the pressure created by the contraction of the ventricle is applied against the upstream surfaces 123. The response is immediate, and the leaflets 105 swing downward from the positions shown in FIG. 3 with the guides 131 simultaneously moving downward in the elongated depressions 111. The downward rotation ends when the downstream edges 145 contact the surfaces 143 of the stops 141 with the guides 131 disposed at the bottom of each of the depressions 111. However, because the leaflets are oriented only slightly offset from the flow path of the blood, there is little force on them in this orientation, and wear is not a problem.

In the open position, as depicted in FIG. 4, and when moving between the open and the closed positions, the relatively flat side surfaces 132 of the guides 131 are nearly aligned with the long dimension of the depressions, and the guides might have a tendency to become canted or offset within the elongated depressions 111. The function of the knobs 137, which are received within the center slots 139, is to eliminate any such tendency and maintain the leaflets always in alignment in the valve body. Because the knobs 137 are entrapped within the center slots, the overall pivoting and translational movement is stabilized, and the guides 131 are positively prevented from moving sideways when the leaflets are in or near the open position orientation. In this respect, there is a sufficient amount of clearance between the exterior surface of the knobs 137 and the interior surface of the center slots (at least about a 5 percent greater radius of curvature) so that the primary pivotal bearing surfaces are the curved terminal surfaces 133 of the guides 131 and the curved interior surface of the depressions 111.

In addition to being elongated, the centering slots 139 are preferably slightly pointed at each end. This pointed configuration, when added to the fact that the knobs 137 move up and down within the centering slots 139, assures a good washing flow of blood through the slots about the exterior surface of the knobs. Likewise, the relatively flat nature of the guides 131, which occupy only a minor portion of the total volume of the depressions at one time, allows entry of blood into the elongated depressions 111 during the time period when the leaflets are in the closed position, and the relative proportioning allows some leakage flow past the curved terminal surfaces 133. This flow, plus the action of pivoting and translational movement back and forth, assures a good flushing of the depressions 111 and the slot 139 and the positive prevention of the build-up of any clotting.

In summary, the combination of the relatively flat guides 131 in the elongated depressions 111 assures good flushing and protection from clotting, and the provision of the small knobs 137 in the centering slots 139 assures stabilization and continuous alignment of the pivoting leaflets 105. Accordingly, this combination is considered to have important advantages in heart valve designs for use both in the aortic and in the mitral positions.

Although the invention has been described with regard to certain preferred embodiments, it should be understood that various modifications and changes as would be obvious to one having the ordinary skill in the art may be made without departing from the scope of the invention which is defined in the appended claims. For example, the depressions 111 might be formed in opposite locations on the leaflets and the guids 131 formed so as to project from the interior surface of the valve body 103.

Various features of the invention are emphasized in the claims which follow.

What is claimed is:

1. A heart valve prosthesis comprising
   an annular valve body having a central passageway therethrough designed to be mounted to permit the flow of blood therethrough in a predetermined downstream direction, and
   a pair of leaflets which are supported for substantially pivotal movement on eccentric axes between a closed position blocking blood flow through said central passageway and an open position allowing blood flow therethrough in said predetermined downstream direction,
   said leaflets and said valve body including projecting guides and depressions which receive said guides,
   said depressions and said projecting guides having complementary surfaces which mount said leaflets in a manner to allow pivotal movement relative to said annular valve body,
   said depressions being elongated so that there is relative rotational and translational movement of said guides within said depressions as said leaflets pivot between the open position and the closed position,
   said guides each having projections which are received in slot means formed as a part of said depressions which maintain a centered alignment of said guides within said depressions during opening and closing movement.

2. A heart valve in accordance with claim 1 wherein said leaflets are curved in cross section having convex surfaces facing upstream and concave surfaces facing downstream.

3. A heart valve in accordance with claim 2 wherein said convex and concave surfaces are spherical.

4. A heart valve in accordance with claim 1 wherein said leaflets are substantially flat.

5. A heart valve prosthesis comprising
   an annular valve body having a central passageway therethrough designed to be mounted to permit the flow of blood therethrough in a predetermined downstream direction,
   a pair of leaflets which are supported for substantially pivotal movement on eccentric axes between a closed position blocking blood flow through said central passageway and an open position allowing blood flow therethrough in said predetermined downstream direction,
   said leaflets and said valve body including projecting guides and depressions which receive said guides,
   said depressions and said projecting guides having complementary surfaces which mount said leaflets in a manner to allow pivotal movement relative to said annular valve body,
   said depressions being elongated so that there is relative rotational and translational movement of said guides within said depressions as said leaflets pivot between the open position and the closed position,
   said guides each having projections which are received in slot means formed as a part of said depressions which maintain alignment of said guides within said depressions during opening and closing movement,
   said guides each having a terminal surface, which is a portion of a spheroidal surface, that is located, between a pair of generally parallel side surfaces, said spheroidal surfaces of said guides defining the pivot axis of each leaflet,
   each guide being formed with a rounded knob which projects from said terminal surface and which is centered on said pivot axis, and
   said depressions each being formed with a surface of substantially mating curvature to said spheroidal surface and with a central elongated slot which is proportioned to receive said rounded knob.

6. A heart valve in accordance with claim 5 wherein said terminal surface is a section of a spherical sector of a predetermined radius and said depressions have surfaces of a radius of curvature slightly greater than said predetermined radius.

7. A heart valve in accordance with claim 6 wherein said knob is a sector of a sphere.

8. A heart valve in accordance with claim 6 wherein said depression has a central section that is a portion of a cylindrical surface of a length equal to at least 10% of said sector radius.

* * * * *